(12) United States Patent
Foster

(10) Patent No.: US 9,050,171 B2
(45) Date of Patent: Jun. 9, 2015

(54) SMALL DIAMETER FRAGMATOME FOR MINIMALLY TRAUMATIC RETAINED LENS FRAGMENTS REMOVAL

(76) Inventor: William J. Foster, Houston, TX (US)

(*) Notice: Subject to any disclaimer, the term of this patent is extended or adjusted under 35 U.S.C. 154(b) by 592 days.

(21) Appl. No.: 13/106,478

(22) Filed: May 12, 2011

(65) Prior Publication Data
US 2012/0083773 A1 Apr. 5, 2012

Related U.S. Application Data

(60) Provisional application No. 61/389,311, filed on Oct. 4, 2010.

(51) Int. Cl.
| | | |
|---|---|---|
| A61B 18/20 | (2006.01) | |
| A61F 9/008 | (2006.01) | |
| A61F 9/007 | (2006.01) | |

(52) U.S. Cl.
CPC ............ *A61F 9/008* (2013.01); *A61F 9/00745* (2013.01); *A61F 2009/0087* (2013.01); *A61F 2009/00887* (2013.01)

(58) Field of Classification Search
CPC ... A61F 9/0061; A61F 9/007; A61F 9/00736; A61F 9/00745; A61F 9/00754; A61F 9/00763; A61F 9/008; A61F 2009/0087
USPC .................. 606/4–6, 10–12, 107; 604/19–28; 128/898
See application file for complete search history.

(56) References Cited

U.S. PATENT DOCUMENTS

| | | | |
|---|---|---|---|
| 3,589,363 A * | 6/1971 | Banko et al. ................. 604/22 |
| 3,693,613 A * | 9/1972 | Kelman ........................ 606/169 |
| 4,002,169 A | 1/1977 | Cupler, II | |
| 4,191,176 A | 3/1980 | Spina | |
| 4,386,927 A | 6/1983 | Eichenbaum | |
| 4,744,360 A | 5/1988 | Bath | |
| 4,908,015 A * | 3/1990 | Anis ................................. 604/22 |
| 5,123,902 A * | 6/1992 | Muller et al. ................... 604/21 |
| 5,242,450 A | 9/1993 | McDonald | |
| 5,451,230 A | 9/1995 | Steinert | |
| 5,674,226 A | 10/1997 | Doherty et al. | |
| 5,738,677 A * | 4/1998 | Colvard et al. ................... 606/4 |
| 5,788,706 A | 8/1998 | Deminski | |
| 6,013,049 A * | 1/2000 | Rockley et al. ................. 604/22 |

(Continued)

OTHER PUBLICATIONS

Kongsap, Pipat, "Combined 20-gauge and 23-gauge pars plana vitrectomy for the management of posteriorly dislocated lens: a case series", Clin. Ophthalmology, pp. 625-628, Jun. 2010.

(Continued)

*Primary Examiner* — Ahmed Farah
(74) *Attorney, Agent, or Firm* — Zeman-Mullen & Ford, LLP

(57) ABSTRACT

A medical instrument is disclosed, comprising a tubular member with proximal and distal ends. The distal end of the tubular member provides an elongated section having a substantially constant outside diameter of no more than 23-gauge (about 0.57 mm). The tubular member is in energy communication with an emulsification energy source disposed to deliver emulsification energy at the distal end of the tubular member. The tubular member may also be in suction communication with a suction source disposed to deliver suction at the distal end of the tubular member. The medical instrument may be used in a method to remove lens fragments from the eye, through incisions in the eye that are small enough not to require suturing after the operation.

2 Claims, 4 Drawing Sheets

(56) References Cited

U.S. PATENT DOCUMENTS

| | | |
|---|---|---|
| 6,217,543 B1 * | 4/2001 | Anis et al. .................. 604/22 |
| 6,299,617 B1 | 10/2001 | Stamler |
| 6,322,557 B1 | 11/2001 | Nikolaevich et al. |
| 6,413,262 B2 | 7/2002 | Saishin et al. |
| 6,544,254 B1 | 4/2003 | Bath |
| 6,605,054 B2 | 8/2003 | Rockley |
| 6,958,056 B2 | 10/2005 | Kadziauskas et al. |
| 7,037,296 B2 | 5/2006 | Kadziauskas et al. |
| 7,329,261 B2 | 2/2008 | Perkins |
| 8,109,937 B2 | 2/2012 | Huculak et al. |
| 2003/0176869 A1 | 9/2003 | Dickerson |
| 2004/0073231 A1 * | 4/2004 | Juan et al. .................. 606/108 |
| 2004/0153093 A1 | 8/2004 | Donovan |
| 2005/0043671 A1 | 2/2005 | Rockley et al. |
| 2006/0036215 A1 | 2/2006 | Boukhny |
| 2006/0155301 A1 | 7/2006 | Holmen |
| 2006/0217739 A1 | 9/2006 | Tjia et al. |
| 2008/0188792 A1 | 8/2008 | Barrett |
| 2010/0228227 A1 | 9/2010 | Krespi et al. |
| 2011/0152745 A1 * | 6/2011 | Castro et al. ................ 604/20 |

OTHER PUBLICATIONS

Arevalo, J., et al., "Current Status of Small-gauge Vitreoretinal Surgery", Retina Today, pp. 42-45, Apr. 2009.

Williams, G. A., "25-, 23-, or 20-guage instrumentation for vitreous surgery?", Eye, pp. 1263-1266, Feb. 2008.

International Search Report and Written Opinion of the International Searching Authority issued in PCT/US2011/052134 and mailed Apr. 13, 2012 and Informal Comments on Written Opinion and International Search Report filed in PCT/US2011/052134 on Jun. 8, 2012.

Gholam A. Peyman, Vitreoretinal Surgical Techniques (2001) at p. 232. This reference may also be seen at Google Books at http://books.google.com/books?id=gEaQ0wiM7JwC&pg=PA232&dq=fragmatome&hl=en&sa=X&ei=GI_TUbWKK_bJ4AOfjoHoBw&ved=0CC8Q6AEwAa#v=onepage&q=fragmatome&f=false.

* cited by examiner

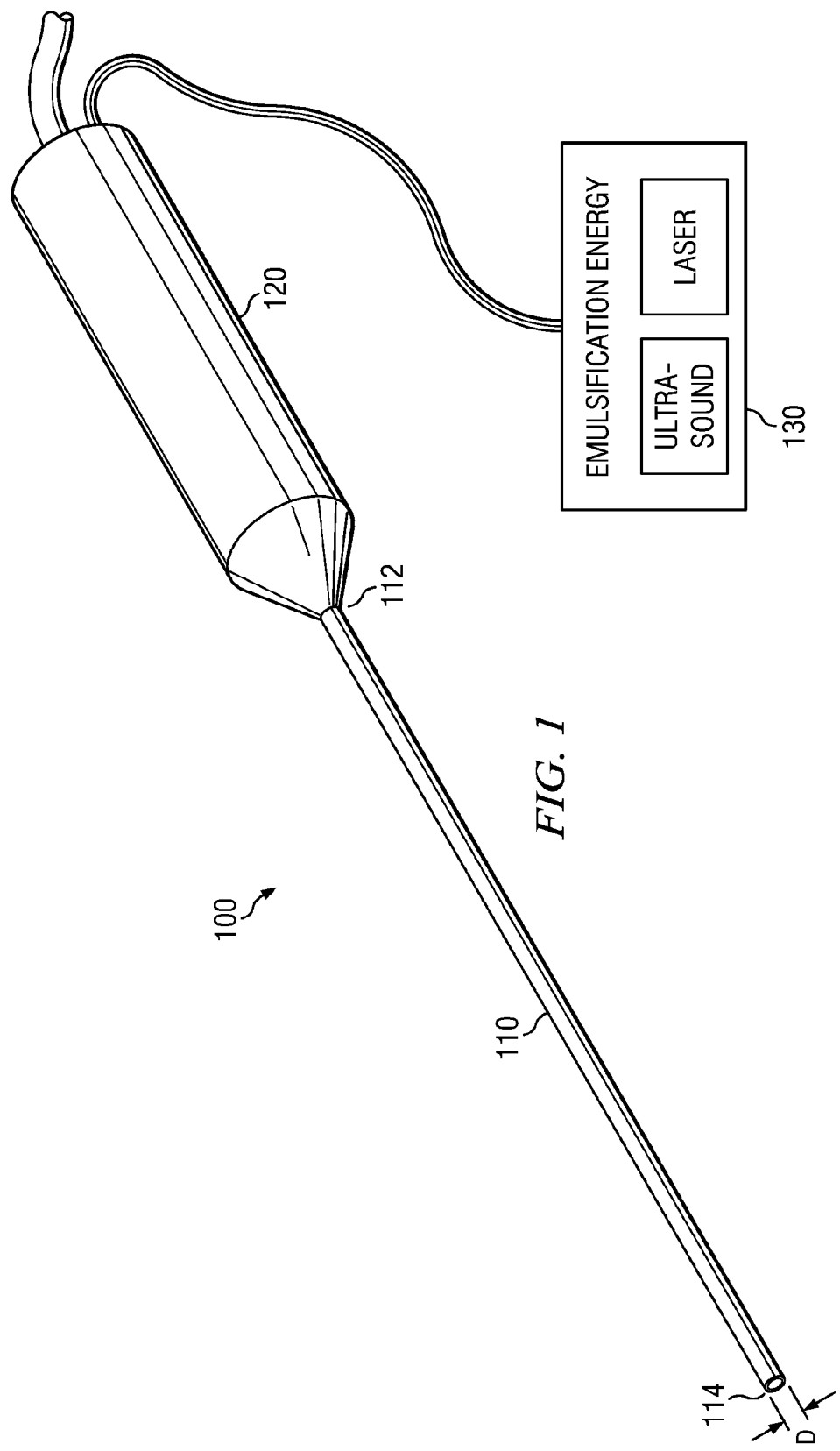

SMALL DIAMETER FRAGMATOME FOR MINIMALLY TRAUMATIC RETAINED LENS FRAGMENTS REMOVAL

CROSS-REFERENCE TO RELATED APPLICATIONS

This application claims the benefit of priority to U.S. provisional patent application No. 61/389,311 filed Oct. 4, 2010, and incorporated herein by reference.

BACKGROUND OF THE INVENTION

The present invention generally relates to eye surgery, and more particularly relates to a method and an apparatus, advantageously a small-diameter fragmatome, for removing retained lens fragments in a minimally traumatic fashion.

During cataract surgery, the natural lens may be removed from inside of the patient's eye. Conventional procedure for removal of the natural lens typically involves making a large (2.9 mm, or larger) incision into the eye and a second, smaller incision. Typically, two incisions are required to accommodate conventional instrumentation into the eye. One incision allows a tubular apparatus (a emulsification tip) into the eye to infuse saline solution to maintain pressure inside the eye and to emulsify and aspirate lens fragments. The second incision allows conventional instrumentation into the eye for various purposes, such as to assist in lens removal. The tubular apparatus emulsifies the lens, typically with ultrasonic or laser energy provided at the tip, causing the natural lens, once lifted toward the front of the eye, to break apart. Application of energy from the tip of the tubular apparatus causes the lens to break down into smaller pieces, small enough to be removed by suction.

It is important to remove all lens fragments before ending the operation. If lens fragments, and especially portions of the center of the lens, also known as the nucleus or the nuclear lens, shift into the back or posterior chamber of the eye, those lens fragments may cause severe trauma (including inflammation and blindness) if left unremoved. Occasionally lens fragments do get left behind, requiring a further procedure for subsequent removal. The conventional procedure is to remove the lens fragments using an additional procedure, by making further incisions into the eye, and removing the remaining lens fragments using a conventional fragmatome. In this additional procedure, three incisions are typically required to accommodate conventional instrumentation into the eye. One incision allows tubular apparatus into the eye to infuse saline solution to maintain vitreous pressure inside the eye. The second incision allows conventional instrumentation into the eye for various purposes, such as to provide light and/or suction. The third incision allows a conventional fragmatome into the eye. The fragmatome emulsifies the lens, typically with ultrasonic or laser energy provided at the tip, causing the lens to break down into smaller pieces, small enough to be removed by suction. Relatively large incisions are suffered by the patient, requiring suturing. Thus, the patient's trauma and healing time is increased.

A drawback to conventional removal of lens fragments from the back of the eye, as described above, is that conventional fragmatomes are comparatively large in design. The tips are typically 20-gauge (about 0.81 mm) in diameter or larger, requiring the incision through which they enter the eye to be correspondingly large. Popular conventional fragmatomes also combine, into one instrument, a tip to provide emulsification energy and a tip to aspirate fragments. This combination causes an even greater potential for a need to introduce a large profile instrument into the eye.

Such large incisions in the eye, as described above to accommodate conventional instrumentation, typically require suturing after the procedure is complete. This suturing, and the healing of the sutured wounds, adds to the trauma suffered by the patient in the operation. Post-operative healing time is also increased.

Current thinking to address some of the above-described drawbacks of conventional surgery to remove lens fragments from the back of the eye appears to focus on miniaturizing the popular combination fragmatome-aspirator, which by its nature has a larger operational profile than either an individual fragmatome or suction tube. Current thinking further appears to be stuck on the notion that emulsification and fragmentation of the removed lens tissue must be done at the same time as removal from the eye of the lens fragments.

Recent professional commentary in the art has recognized a long felt but unsolved need for apparatus and methods for removing lens fragments using a small gauge fragmatome, advantageously 23-gauge (about 0.57 mm) or smaller in operative diameter. In his article "Combined 20-gauge and 23-gauge pars plana vitrectomy for the management of posteriorly dislocated lens: a case series" (published in the 18 Jun., 2010 edition of the professional magazine "Clinical Ophthalmology"), P. Kongsap teaches that small gauge instrumentation (typically 23-gauge or smaller) may enter the eye cavity though incisions small enough not to require suturing, minimizing trauma to the patient and reducing recovery time. However, when lens fragments are left in the posterior eye cavity, removal of those fragments through those same small incisions is made difficult by the unavailability of a small gauge (23-gauge or less) fragmatome.

As can be seen, there is a need for a method and an apparatus for removing lens fragments from the eye in a minimally traumatic fashion, and in particular using a small gauge fragmatome entering the eye through smaller incisions that will not require suturing. An improved method using such a small gauge fragmatome could also reduce patient trauma and post-operative healing time.

SUMMARY OF THE INVENTION

The present invention addresses one or more of the above-described drawbacks of the prior art. One aspect of this invention includes a medical instrument comprising a tubular member with proximal and distal ends. The distal end of the tubular member provides an elongated section having a substantially constant outside diameter of no more than 23-gauge (about 0.57 mm). The medical device further comprises a handle connected to the proximal end of the tubular member. The tubular member is in energy communication with an emulsification energy source disposed to deliver emulsification energy at the distal end of the tubular member. In presently preferred embodiments, the emulsification energy is selected from the group consisting of ultrasound energy and laser energy, but the invention is not limited in this regard. The tubular member may also be in suction communication with a suction source disposed to deliver suction at the distal end of the tubular member.

Another aspect of this invention includes a method for removing at least one lens fragment from within an eye, the method comprising the steps of: (a) making incisions in the eye, each incision no larger than about 0.8 mm; (b) inserting a fragmatome through a first one of the incisions, the fragmatome no larger than 23-gauge; (c) using the fragmatome to emulsify the at least one lens fragment into a plurality of emulsified fragments; and (d) aspirating ones of the plurality of emulsified fragments from the eye.

In one variation on the method, step (b) further includes the substep of inserting a trochar into the first one of the incisions prior to inserting the fragmatome therethrough, the trochar suitable to port instrumentation of a diameter of at least 23-gauge.

In another variation on the method, step (d) includes the substeps of (i) withdrawing the fragmatome and then inserting a vitrector through the first one of the incisions, the vitrector no larger than 23-gauge, and (ii) using the vitrector to aspirate ones of the plurality of emulsified fragments from the eye.

In another variation, step (d) includes the substeps of (i) withdrawing the fragmatome and then inserting a suction tube through the first one of the incisions, the suction tube no larger than 23-gauge, and (ii) using the suction tube to aspirate ones of the plurality of emulsified fragments from the eye.

In another variation, step (b) further includes, prior to inserting the fragmatome through the first one of the incisions, the substeps of (i) inserting a vitrector through the first one of the incisions, the vitrector no larger than 23-gauge, (ii) using the vitrector to aspirate vitreous from around the at least one lens fragment, and (iii) withdrawing the vitrector from the first one of the incisions.

In another variation, step (c) further includes the substep of impaling the at least one lens fragment with the fragmatome prior to using the fragmatome to emulsify the at least one lens fragment.

It is therefore a technical advantage of the invention to enter the eye with a fragmatome capable of being inserted through incisions small enough not to require suturing after the operation. An exemplary application of such a fragmatome is in a method for removing lens tissue fragments from the vitreous cavity of the eye.

A further technical advantage of the invention is that trauma to the patient as a result of the operation is reduced, and recovery time is improved.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should be also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 illustrates a fragmatome in accordance with one aspect of the present invention;

DETAILED DESCRIPTION OF THE INVENTION

Figure 2A:
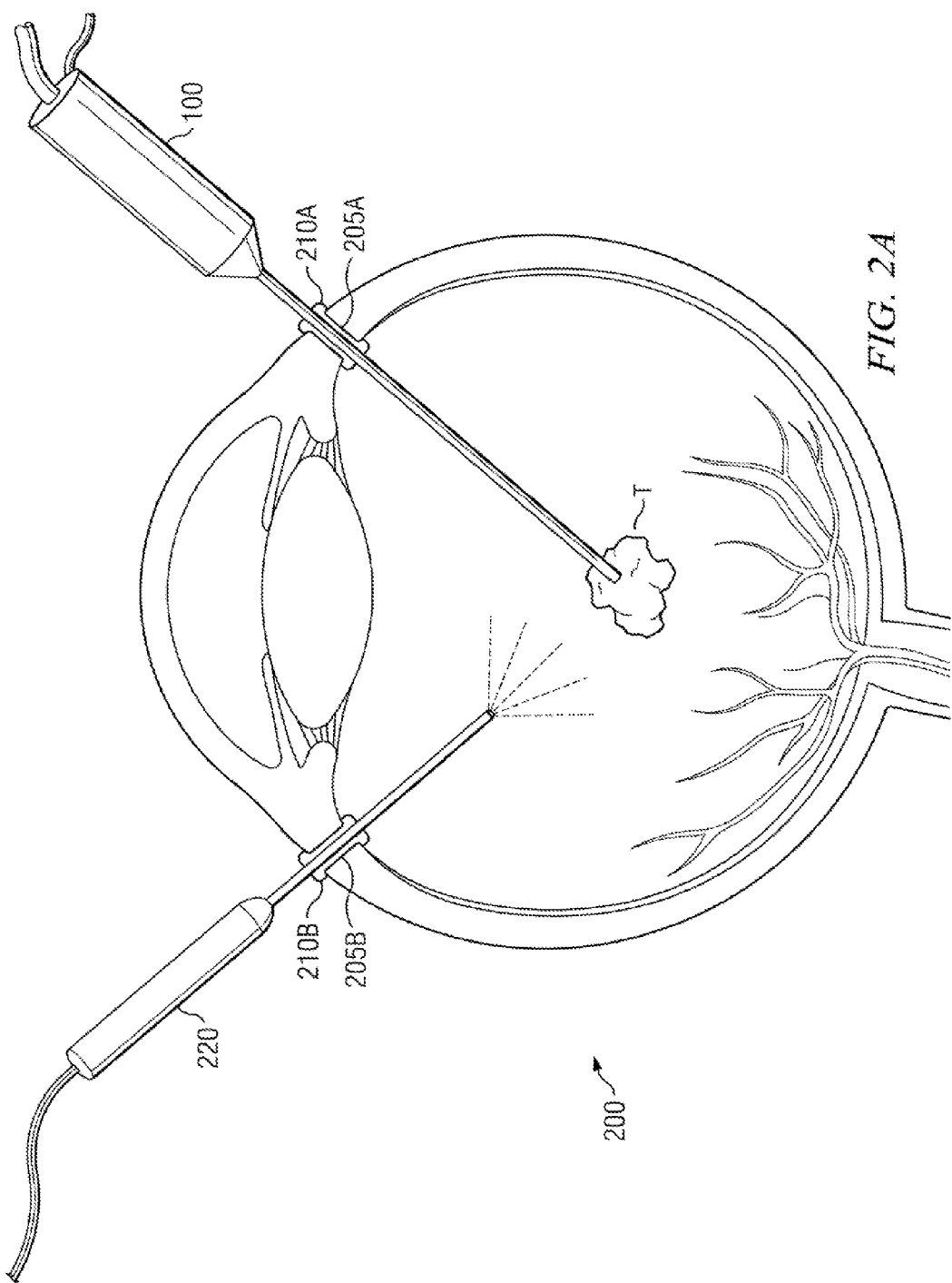
FIG. 2A illustrates a first phase of a method in accordance with a second aspect of the present invention.

FIG. 1 is an outline illustration of a fragmatome 100 in accordance with a first aspect of the present invention. Fragmatome 100 comprises a tubular member 110 with a substantially constant outside diameter D. Tubular member 100 provides proximal end 112 and distal end 114. Fragmatome 100 may be constructed conventionally. However, in accordance with the invention, D is no more than 23-gauge (about 0.57 mm) in diameter. With further reference to FIG. 1, handle 120 is attached to a proximal end 112. Box 130 on FIG. 1 is a functional representation of an emulsification energy source to which fragmatome 100 is configured/capable of being connected. Although not specifically illustrated, it will be understood that fragmatome 100 is disposed to deliver emulsification energy at distal end 114. As illustrated via box 130, such emulsification energy may be, for example and without limitation, ultrasonic energy or laser energy. The source of emulsification energy may be conventional, and may be deployed in handle 120 or elsewhere in emulsification energy communication with distal end 114.

FIG. 1 shows tubular member 110 being of substantially constant diameter D, but it will be appreciated that the invention is not limited in this regard. In an embodiment not illustrated, but consistent with the invention, an elongated length of tubular member 110 at distal end 114 may have outside diameter D, while a portion of the remaining length of tubular member 110 towards proximal end 112 may have a different diameter.

It will be further appreciated that in some embodiments of fragmatome 100 as illustrated on FIG. 1, distal end 114 may be disposed to deliver suction. The suction source may be conventional, and again may be deployed in handle 120 or elsewhere in suction communication with distal end 114.

Figure 2B:
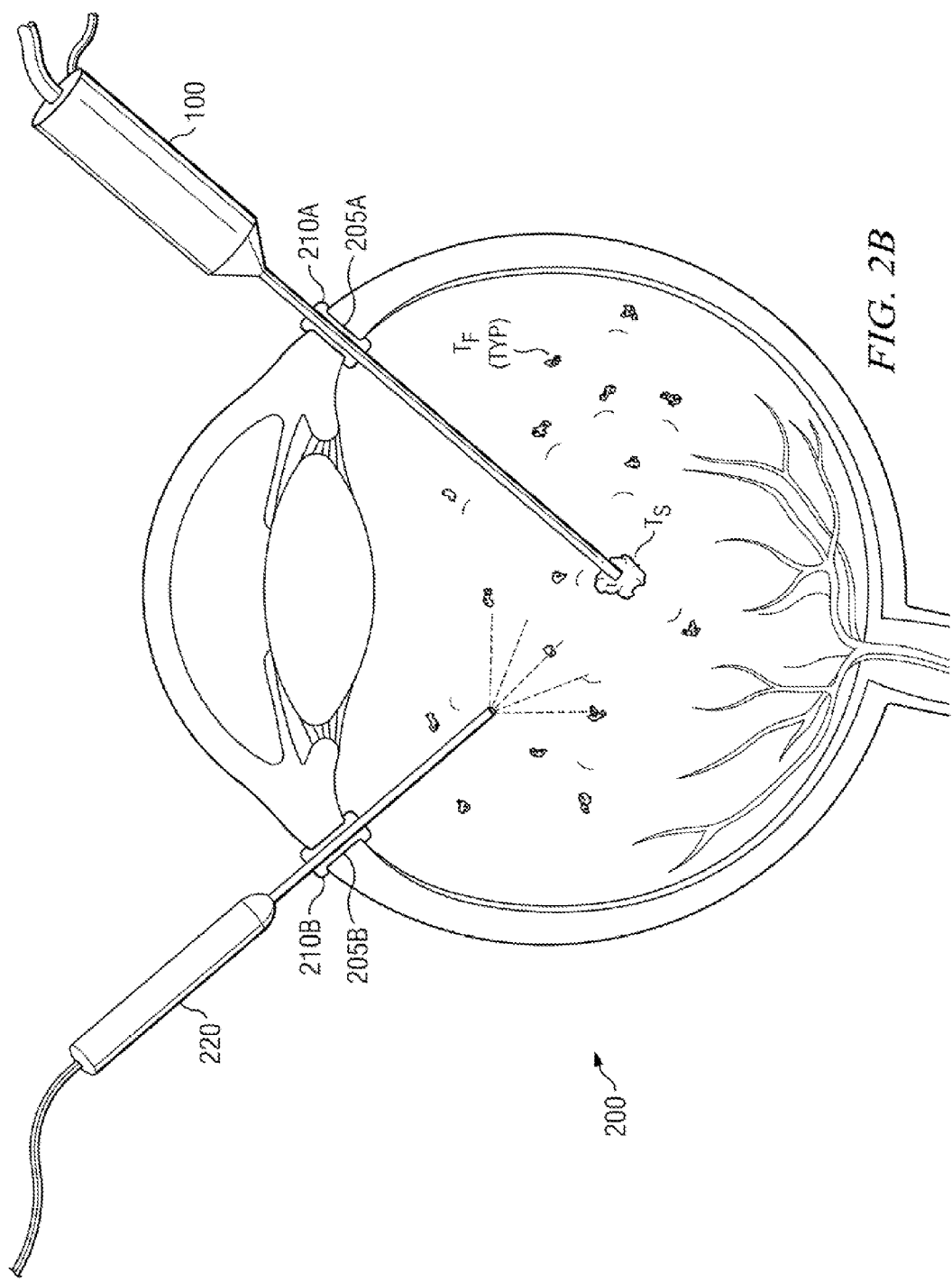
FIG. 2B illustrates a second phase of a method in accordance with a second aspect of the present invention.
Figure 2C:
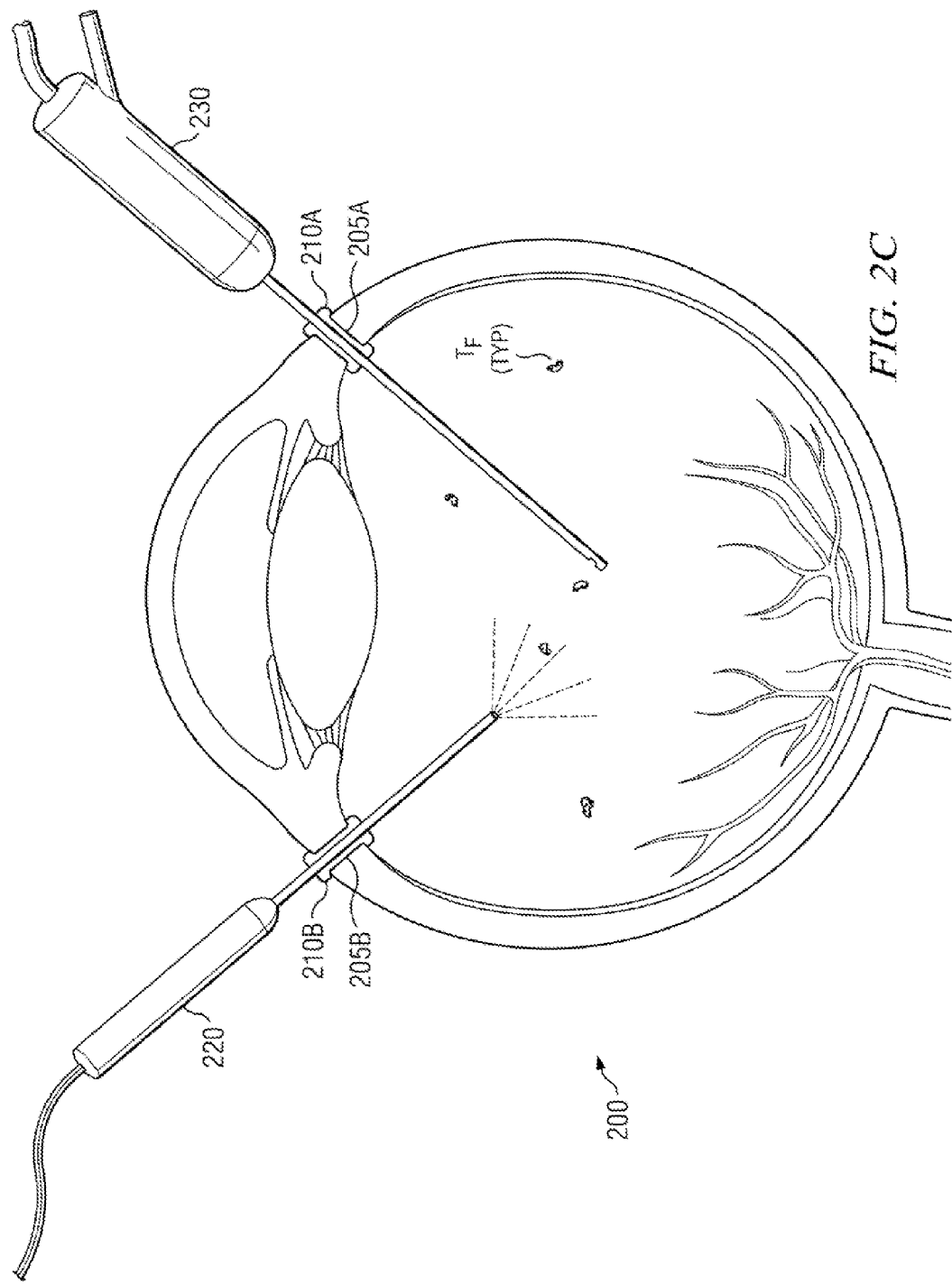
FIG. 2C illustrates a third phase of a method in accordance with a second aspect of the present invention.

FIGS. 2A through 2C each illustrate, respectively, first, second and third phases of a method in accordance with a second aspect of the present invention. It will be appreciated that the embodiment of the method as set forth in FIGS. 2A through 2C is one exemplary application (and, at this time, a preferred application) for the fragmatome disclosed herein, an embodiment of which was described above with reference to FIG. 1. It will be further appreciated that the fragmatome disclosed herein is suitable for use in other methods, in addition to the method set forth with reference to FIGS. 2A through 2C.

Turning to a first phase of the method in accordance with a second aspect of the invention, and as illustrated in FIG. 2A, fragmatome 100 from FIG. 1 (as described above) is in use in the vitreous cavity of an eye 200. In FIG. 2A, two surgical incisions 205A and 205B have been made through the sclera into the vitreous cavity. It will be understood that consistent with the invention, incisions 205A and 205B are large enough to allow 23-gauge or smaller instrumentation through into the vitreous cavity, but small enough not to require suturing after the operation is complete. It will be understood that nominally, according to current technology, such an incision size is no larger than about 0.8 mm. Optionally, and as illustrated on FIG. 2A, trochars 210A and 210B are deployed, one each in incisions 205A and 205B, and through which 23-gauge or smaller instrumentation may be ported.

It will be appreciated that, consistent with the invention described with reference to FIGS. 2A through 2C, a third incision is also made into the eye. This third incision has not been illustrated on FIGS. 2A through 2C for the sake of clarity. This third incision is, consistent with incisions 205A and 205B on FIG. 2A, also large enough to allow 23-gauge or smaller instrumentation through into the vitreous cavity, but small enough not to require suturing after the operation is complete (such an incision size again, according to current technology, no larger than about 0.8 mm). It will be appreciated that a conventional infusion cannula is inserted into the eye through the third incision and resides there throughout the method described with reference to FIGS. 2A through 2C. The infusion cannula is operable to maintain vitreous pressure in the eye during the method. Optionally, a trochar may also deployed in the third incision prior to insertion of the infusion cannula, the trochar suitable to port 23-gauge or smaller instrumentation.

With further reference to FIG. 2A, a conventional 23-gauge light pipe 220 is inserted through either one of trochars 210A or 210B (through trochar 210B as illustrated). Light pipe 220 is operable to illuminate the vitreous cavity. Fragmatome 100 (as described above with reference to FIG. 1) is inserted through the other trochar (through trochar 210A as illustrated) and into the vitreous cavity. As shown on FIG. 2A, fragmatome is disposed to operate on lens tissue sample T found in the vitreous cavity. It will be appreciated that lens tissue sample T may, without limitation, have been lifted from the surface of the retina using suction delivered through fragmatome 100, or through a separate suction tube (not illustrated), or alternatively may have been already floating in the vitreous cavity when encountered by fragmatome 100. In another technique (not illustrated), lens tissue sample T may have been impaled by a solid pin or by fragmatome 100 and withdrawn away from the retina while still impaled. It will be further appreciated that as illustrated on FIG. 2A, lens tissue sample T is too large to be withdrawn from the vitreous cavity through 23-gauge instrumentation.

Turning now to FIG. 2B, a second phase of a method in accordance with a second aspect of the present invention is illustrated. It will be appreciated that in FIG. 2B, the items and part numbers as illustrated and labeled on FIG. 2B are the same as the corresponding items and part numbers on FIG. 2A, with the exception of lens tissue sample T. In FIG. 2B, fragmatome 100 has operated on lens tissue sample T (from FIG. 2A) to now present a smaller lens tissue sample $T_S$ (as shown on FIG. 2B). More specifically, in the passage from FIG. 2A to FIG. 2B, fragmatome 100 has delivered emulsification energy to lens tissue sample T (from FIG. 2A) so that, as illustrated in FIG. 2B, lens tissue sample T (from FIG. 2A) is broken down into a smaller lens tissue $T_S$ and a plurality of lens tissue fragments $T_F$. In the technique described in the previous paragraph (not illustrated) where lens tissue sample T is impaled by fragmatome 100, it will be appreciated that delivery of emulsification energy to the fragmatome will cause breakdown of lens tissue sample T into smaller fragments while still impaled. It will also be understood that lens fragments $T_F$ are created by fragmatome 100 to be small enough to be able to be withdrawn from the vitreous cavity through 23-gauge instrumentation.

Turning now to FIG. 2C, and continuing on to a third phase of a method whose first and second phases are described above with reference to FIGS. 2A and 2B, it will be appreciated that fragmatome 100 (from FIGS. 1, 2A and 2B) has now been used to break lens tissue sample T (from FIG. 2A) and $T_S$ (from FIG. 2B) all the way down to a plurality of lens fragments $T_F$. For the avoidance of doubt, the items and part numbers as illustrated and labeled on FIG. 2C are the same as the corresponding items and part numbers on FIG. 2B, except that fragmatome 100 on FIG. 2B has been withdrawn on FIG. 2C and replaced with vitrector 230. Vitrector 230 is of conventional manufacture and in FIG. 2C, consistent with other instrumentation illustrated on FIGS. 2A through 2C, is no larger than 23-gauge. In FIG. 2C, lens fragments $T_F$ are being aspirated from the vitreous cavity through vitrector 230.

In a variation on the method described with reference to FIGS. 2A through 2C (not illustrated), fragmatome 100 may be left in place after emulsification of lens tissue sample T and $T_S$ into lens fragments $T_F$, and lens fragments $T_F$ may then be aspirated from the vitreous cavity using suction capability within fragmatome 100. In a further variation (not illustrated), fragmatome 100 may be withdrawn after emulsification of lens tissue sample T and $T_S$ into lens fragments $T_F$, and replaced by other conventional tubular suction instrumentation with which to aspirate lens fragments $T_F$ from the vitreous cavity. In yet another variation (not illustrated), vitrector 230 may be inserted prior to insertion of fragmatome 100, for the purpose of aspirating vitreous from around lens tissue sample T prior to emulsification by fragmatome 100.

It should be understood, of course, that the foregoing relates to exemplary embodiments of the invention and that modifications may be made without departing from the spirit and scope of the invention as set forth in the following claims.

I claim:

1. A fragmatome for eye tissue removal, comprising:
   a tubular fragmatome needle with proximal and distal ends, the fragmatome needle providing a lumen therethrough;
   the distal end of the fragmatome needle providing an elongated section thereof, the elongated section of the fragmatome needle having a constant outside diameter of no more than 23-gauge;
   a fragmatome handle connected to the proximal end of the fragmatome needle;
   the fragmatome needle configured to be connected to an emulsification source, and when connected to the emulsification energy source, delivering emulsification energy at the distal end of the fragmatome needle; and
   the lumen configured to be connected to a suction source, and when connected to the suction source, delivering suction at the distal end of the fragmatome needle;
   the fragmatome needle further configured to deliver, at the distal end thereof, emulsification energy at selected times concurrently with said delivery of suction by the lumen.

2. The fragmatome of claim 1, in which said emulsification energy is selected from the group consisting of:
   (a) ultrasound energy; and
   (b) the laser energy.

* * * * *